US006849407B2

(12) United States Patent
Espy et al.

(10) Patent No.: US 6,849,407 B2
(45) Date of Patent: Feb. 1, 2005

(54) DETECTION OF VARICELLA-ZOSTER VIRUS

(75) Inventors: Mark J. Espy, Rochester, MN (US); Jim Uhl, Rochester, MN (US); Thomas F. Smith, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/945,203

(22) Filed: Aug. 31, 2001

(65) Prior Publication Data

US 2002/0182634 A1 Dec. 5, 2002

Related U.S. Application Data

(60) Provisional application No. 60/229,499, filed on Aug. 31, 2000.

(51) Int. Cl.[7] ............................. C12Q 1/68; C12P 19/34; C07H 21/02; C07H 2/04

(52) U.S. Cl. .......................... 435/6; 435/91.1; 435/91.2; 536/23.1; 536/24.1; 536/23.7; 536/24.32

(58) Field of Search ........................... 435/6, 91.1, 91.2; 536/23.1, 24.1, 23.7, 24.32

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,800,159 A | | 1/1989 | Mullis et al. |
| 4,965,188 A | | 10/1990 | Mullis et al. |
| 5,702,895 A | | 12/1997 | Matsunaga et al. |
| 5,925,733 A | * | 7/1999 | Rose et al. .................. 530/350 |
| 6,174,670 B1 | * | 1/2001 | Wittwer et al. ................ 435/6 |

FOREIGN PATENT DOCUMENTS

| | | |
|---|---|---|
| EP | 0 526 876 | 2/1993 |
| EP | 1 045 033 | 10/2000 |
| EP | 1 160 333 | 12/2001 |
| JP | 7-199 | 1/1995 |
| WO | WO 97/46707 | 12/1997 |
| WO | WO 97/46712 | 12/1997 |
| WO | WO 97/46714 | 12/1997 |
| WO | WO 98/48046 | 10/1998 |
| WO | WO 01/12803 | 2/2001 |
| WO | WO 01/23604 | 4/2001 |
| WO | WO 03/068918 | 8/2003 |

OTHER PUBLICATIONS

Davison et al. J. gen. Virol. (19986) 67, 1759–1816.*
Beards et al. Journal of Medical Virology 54: 155–157 (1998).*
Longo et al. Gene 93 (1990) 125–128.*
SeqAlignments for SEQID Nos 1–8 w/ Davison Reference & SEQID Nos 1–4 w/ Rose et al.*

Bassler et al., "Use of a Fluorogenic Probe in a PCR–Based Assay for the Detection of *Listeria monocytogenes,*" *Applied amd Environmental Microbiology*, 1995, 61(10):3724–3728.

Davison and Scott, "The Complete DNA Sequence of Varicella–Zoster Virus," *J. Gen. Virol.*, 1986, 67:1759–1816.

De Silva et al., "Rapid Genotyping and Quantification on the LightCycler with Hybridization Probes," *Biochemica*, 1998, 2:12–15.

Espy et al., "Diagnosis of Herpes Simplex Virus Infections in the Clinical Laboratory by LightCycler PCR," *J. Clin. Microbiol.*, 2000, 38:795–799.

Espy et al., "Diagnosis of Varicella–Zoster Virus Infections in the Clinical Laboratory by LightCycler PCR," *J. Clin. Microbiol.*, 2000, 38(9):3187–3189.

Hawrami and Breuer, "Development of a flurogenic polymerase chain reaction assay (TaqMan) for the detection and quantitation of varicella zoster virus," *J. Virol. Methods*, 1999, 79:33–40.

Kimura et al., "Recombinant Varicella–Zoster Virus Glycoproteins E and I: Immunologic Responses and Clearance of Virus in a Guinea Pig Model of Chronic Uveitis," *J. Infect Dis.*, 1998, 178:310–317.

Kimura et al., "Comparison of Quantitations of Viral Load in Varicella and Zoster," *J. Clin. Microbiol.*, 2000, 38:2447–2449.

Pevenstein et al., "Quantitation of Latent Varicella–Zoster Virus and Herpes Simplex Virus Genomes in Human Trigeminal Ganglia," *J. Virol.*, 1999, 73:10514–10518.

Sauerbrei et al., "Laboratory diagnosis of herpes zoster," *J. Clin. Virol.*, 1999, 14:31–36.

GenBank Accession No. M14891 Complete Genome.
GenBank Accession No. M16612.
GenBank Accession No. X04370 Complete Genome.

Bouquillon et al., "Simultaneous Detection of 6 Human Herpesviruses in Cerebrospinal Fluid and Aqueous Fluid by a Single PCR Using Stair Primers," *J. Med. Virol.*, 2000, 62:349–353.

Brinker and Doern, "Comparsion of MRC–5 and A–549 Cells in Conventional Culture Tubes and Shell Vial Assays for the Detection of Varicella–Zoster Virus," *Diagn. Microbiol. Infect. Dis.*, 1993, 17:75–77.

Coffin and Hodinka, "Utility of Direct Immunoflourescence and Virus Culture for Detection of Varicella–Zoster Virus in Skin Lesions," *J. Clin. Microbiol.*, 1995, 33(10):2792–2795.

(List continued on next page.)

Primary Examiner—Carla J. Myers
Assistant Examiner—Sally Sakelaris
(74) Attorney, Agent, or Firm—Fish & Richardson P.C., P.A.

(57) ABSTRACT

The invention provides methods to detect VZV in biological samples using real-time PCR. Primers and probes for the detection of VZV are provided by the invention. Articles of manufacture containing such primers and probes for detecting VZV are further provided by the invention.

43 Claims, No Drawings

OTHER PUBLICATIONS

Cowl et al., "Varicella–Zoster Virus Detection by Polymerase Chain Reaction Using Bronchoalveolar Lavage Specimens," *Am. J. Respir. Crit. Care Med.*, 2000, 161:753–754.

de Jong et al., "Quantitation of Varicella–Zoster Virus DNA in Whole Blood, Plasma, and Serum by PCR and Electrochemiluminescence," *J. Clin. Microbiol.*, 2000, 38(7):3568–2573.

Espy et al., "Diagnosis of Herpes Simplex Virus Infections in the Clinical Laboratory by LightCycler PCR," *J. Clin. Microbiol.*, 2000, 38(2):795–799.

Espy et al., "Diagnosis of Varicella–Zoster Virus Infections in the Clinical Laboratory by LightCycler PCR," *J. Clin. Microbiol.*, 2000, 38(9):3187–3189.

Kimura et al., "Recombinant Varicella–Zoster Virus Glycoproteins E and I: Immunologic Responses and Clearance of Virus in a Guinea Pig Model of Chronic Uveitis," *J. Infect. Dis.*, 1998, 178:310–317.

Kimura et al., "Comparison of Quantitations of Viral Load in Varicella and Zoster," *J. Clin. Microbiol.*, 2000, 38(6):2447–2449.

Loparev et al., "Improved Identification and Differentiation of Varicella–Zoster Virus (VZV) Wild–Type Strains and an Attenuated Varicella Vaccine Strain Using a VZV Open Reading Frame 62–Based PCR," *J. Clin. Microbiol.*, 2000, 38(9):3156–3160.

McCarter and Ratkiewicz, "Comparison of Virus Culture and Direct Immunofluorescent Staining of Cytocentrifuged Virus Transport Medium for Detection of Varicella–Zoster Virus in Skin Lesions," *Am. J. Clin. Pathol.*, 1998, 109:631–633.

Pitkäranta et al., "Detection of Human Herpesvirus 6 and Varicella–Zoster Virus in Tear Fluid of Patients with Bell's Palsy by PCR," *J. Clin. Microbiol.*, 2000, 38(7):2753–2755.

Sauerbrei et al., "Laboratory diagnosis of herpes zoster," *J. Clin. Virol.*, 1999, 14:31–36.

Schirm et al., "Rapid Detection of Varicella–Zoster Virus in Clinical Specimens Using Monoclonal Antibodies on Shell Vials and Smear," *J. Med. Virol.*, 1989, 28:1–6.

van Gelderen et al., "Detection of herpes simplex virus type 1,2 and varicella zoster virus DNA in recipient corneal buttoms," *Br. J. Ophthalmol.*, 2000, 84:1238–1243.

Yamamoto and Nakamura, "A single tube PCR assay for simultaneous amplification of HSV–1/–2, VZV, CMV, HHV–6A/–6B, and EBV DNAs in cerbrospinal fluid from patients with virus–related neurological diseases," *J. Neuro Virol.*, 2000, 6:410–417.

Arthur et al., "Enterococcus faccium transposon Tn1546 transposase, resolvase, vanR, vanS, vanH, vanA, vanX, vanY and teicoplanin resistance protein (vanZ) genes, complete cds," 1993, database accession No. M97297.

Grisold et al., "Detection of Methicillin–Resistant *Staphylococcus aureus* and Simultaneous Confirmation by Automated Nucleic Acid Extraction and Real–Time PCR," *J. Clin. Microbiol.*, 2002, 40:2392–2397.

Huletsky et al., "Rapid Detection of Vancomycin–Resistant Enterococci Directly from Rectal Swabs by Real–Time PCR Using the Smart Cycler," *Abstracts of the Interscience Conference on Antimicrobial Agents and Chemotherapy*, Chicago, Illinois, Sep. 22–25, 2001, 41:409 (Abstract K–1195).

Ito et al., "*Staphylococcus aureus* DNA, type–I staphylococcal cassette chromosome mec," 1999, database accession No. AB033763.

"LightCycler–FastStart DNA Master Hybridization Probes," 1999 Roche Diagnostics GMbH Technical Manual, retrieved from the internet on Feb. 6, 2004: http://www.roche–applied–science.com.

Palladino et al., "Real–time PCR for the rapid detection of *vanA* and *vanB* genes," *Diagnostic Microbiology and Infectious Disease*, 2003, 45:81–84.

Palladino et al., "Rapid Detection of *vanA* and *vanB* Genes Directly from Clinical Specimens and Enrichment Broths by Real–Time Multiplex PCR Assay," *J. Clin. Microbiol.*, 2003, 41:2483–2486.

Patel et al., "*Enterococcus faecium* vancomycin resistance protein vanB gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of *vanA* and *vanB* genes in clinical specimens for rapid identification of vancomycin resistant enterococci (VRE) using multiplex PCR," *Molecular and Cellular Probes*, 1999, 13:275–281.

Reischul et al., "Rapid Identification of Methicillin–Resistant *Staphylococcus aureus* and Simultaneous Species Confirmation Using Real–Time fluorescence PCR," *J. Clin. Microbiol.*, 2000, 38:2429–2433.

Sloan et al., "Evaluation of a Combined LightCycler Assay for the Detection of vanA, vanB, and vanB–2/3 Genes in Enterococci," *Abstracts of the General Meeting of the American Society for Microbiology*, 2002, 102:143 (Abstract C–242).

Al–Robaiy et al., "Rapid Competitive PCR Using Melting Curve Analysis for DNA Quantification," *BioTechniques*, 2001, 31:1382–1388.

Bélanger et al., "Rapid Detection of Shiga Toxin–Producing Bacteria in Feces by Multiplex PCR with Molecular Beacons on the Smart Cycler," *J. Clin. Microbiol.*, 2002, 40:1436–1440.

Bellin et al., "Rapid Detection of Enterohemorrhagic *Escherichia coli* by Real–Time PCR with Fluorescent Hybridization Probes," *J. Clin. Microbiol.*, 2001, 39:370–374.

Chen et al., An Automated Fluorescent PCR Method for Detection of Shiga Toxin–Producing *Escherichia coli* in Foods: *Appl. Environ. Microbiol.*, 1998, 64:4210–4216.

Didenko, "DNA Probes Using Fluorecence Resonance Energy Transfer (FRET): Designs and Applications," *BioTechniques* 2001, 31:1106–1121.

Ramotar et al., "Direct Detection of Verotoxin–Producing *Eschericha coli* in Stool Samples by PCR," *J. Clin. Microbiol.*, 1995, 33:519–524.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357–362.

* cited by examiner

SEQUENCE LISTING

<160> NUMBER OF SEQ ID NOS: 8

<210> SEQ ID NO 1
<211> LENGTH: 25
<212> TYPE: DNA
<213> ORGANISM: Artificial sequence
<220> FEATURE:
<223> OTHER INFORMATION: Synthetically generated oligonucleotide

<400> SEQUENCE: 1
gacaatatca tatacatgga atgtg                                          25

<210> SEQ ID NO 2
<211> LENGTH: 23
<212> TYPE: DNA
<213> ORGANISM: Artificial sequence
<220> FEATURE:
<223> OTHER INFORMATION: Synthetically generated oligonucleotide

<400> SEQUENCE: 2
gcggtagtaa cagagaattt ctt                                            23

<210> SEQ ID NO 3

-continued

```
<211> LENGTH: 25
<212> TYPE: DNA
<213> ORGANISM: Artificial sequence
<220> FEATURE:
<223> OTHER INFORMATION: Synthetically generated oligonucleotide

<400> SEQUENCE: 3
cgaaaatcca gaatcggaac ttctt                                          25

<210> SEQ ID NO 4
<211> LENGTH: 25
<212> TYPE: DNA
<213> ORGANISM: Artificial sequence
<220> FEATURE:
<223> OTHER INFORMATION: Synthetically generated oligonucleotide

<400> SEQUENCE: 4
ccattacagt aaactttagg cggtc                                          25

<210> SEQ ID NO 5
<211> LENGTH: 23
<212> TYPE: DNA
<213> ORGANISM: Artificial sequence
<220> FEATURE:
<223> OTHER INFORMATION: Synthetically generated oligonucleotide

<400> SEQUENCE: 5
tgtcctagag gaggttttat ctg                                            23

<210> SEQ ID NO 6
<211> LENGTH: 23
<212> TYPE: DNA
<213> ORGANISM: Artificial sequence
<220> FEATURE:
<223> OTHER INFORMATION: Synthetically generated oligonucleotide

<400> SEQUENCE: 6
catcgtctgt aagacttaac cag                                            23

<210> SEQ ID NO 7
<211> LENGTH: 28
<212> TYPE: DNA
<213> ORGANISM: Artificial sequence
<220> FEATURE:
<223> OTHER INFORMATION: Synthetically generated oligonucleotide

<400> SEQUENCE: 7
gggaaatcga gaaaccaccc tatccgac                                       28

<210> SEQ ID NO 8
<211> LENGTH: 27
<212> TYPE: DNA
<213> ORGANISM: Artificial sequence
<220> FEATURE:
<223> OTHER INFORMATION: Synthetically generated oligonucleotide

<400> SEQUENCE: 8
aagttcgcgg tataattgtc agtggcg                                        27
```

DETECTION OF VARICELLA-ZOSTER VIRUS

CROSS REFERENCE TO RELATED APPLICATIONS

This application claims priority under 35 U.S.C. §119(e) of U.S. provisional application Ser. No. 60/229,499, filed Aug. 31, 2000.

TECHNICAL FIELD

This invention relates to viral diagnostics, and more particularly to detection of varicella-zoster virus (VZV).

BACKGROUND

The most common dermal manifestation resulting from primary infection with varicella-zoster virus (VZV) is chickenpox (varicella), which generally occurs in early childhood. Reactivation of latent virus occurs in about 10–20% of adults and produces vesicles that are typically confined to a single dermatome of the skin (herpes zoster). VZV infections can cause systemic infections of the central nervous and respiratory systems in immunologically competent patients and produce disseminated disease of multiple organ systems in those with impaired immunologic defenses. Laboratory diagnosis is important for distinguishing herpes simplex virus (HSV) from VZV infections since clinical presentation of herpes zoster due to VZV can be confused with the dermal distribution produced by HSV.

SUMMARY

The invention provides for methods of identifying varicella-zoster virus (VZV) in a biological sample. Primers and probes for detecting VZV are provided by the invention, as are kits containing such primers and probes. Methods of the invention can be used to rapidly identify VZV DNA from specimens for diagnosis of VZV infection and to differentiate VZV infections from HSV infections. Using specific primers and probes, the methods include amplifying and monitoring the development of specific amplification products using fluorescence resonance energy transfer (FRET).

In one aspect of the invention, there is provided a method for detecting the presence or absence of VZV in a biological sample from an individual. The method to detect VZV includes performing at least one cycling step, which includes an amplifying step and a hybridizing step. The amplifying step includes amplifying a portion of a VZV gene 28 nucleic acid molecule from the biological sample using a pair of gene 28 primers, thereby producing a gene 28 amplification product. The hybridizing step includes annealing a pair of gene 28 probes to the gene 28 amplification product. Generally, the members of the pair of gene 28 probes hybridize within no more than five nucleotides of each other. A first gene 28 probe of the pair of gene 28 probes is typically labeled with a donor fluorescent moiety and a second gene 28 probe of the pair of gene 28 probes is labeled with a corresponding acceptor fluorescent moiety. The method further includes detecting the presence or absence of FRET between the donor fluorescent moiety of the first gene 28 probe and the acceptor fluorescent moiety of the second gene 28 probe upon hybridization of the pair of gene 28 probes to the amplification product. The presence of FRET is usually indicative of the presence of VZV in the biological sample, while the absence of FRET is usually indicative of the absence of VZV in the biological sample.

Alternatively, the amplifying step includes amplifying a portion of a VZV gene 29 nucleic acid molecule from the biological sample using a pair of gene 29 primers, thereby producing a gene 29 amplification product. The hybridizing step includes annealing a pair of gene 29 probes to the gene 29 amplification product. Generally, the members of the pair of gene 29 probes hybridize within no more than five nucleotides of each other. A first gene 29 probe of the pair of gene 29 probes is typically labeled with a donor fluorescent moiety and a second gene 29 probe of the pair of gene 29 probes is labeled with a corresponding acceptor fluorescent moiety. The method further includes detecting the presence or absence of FRET between the donor fluorescent moiety of the first gene 29 probe and the acceptor fluorescent moiety of the second gene 29 probe upon hybridization of the pair of gene 29 probes to the gene 29 amplification product. The presence of FRET is usually indicative of the presence of VZV in the biological sample, while the absence of FRET is usually indicative of the absence of VZV in the biological sample. The methods to detect VZV using gene 28 and gene 29 can be performed individually, sequentially or concurrently.

A pair of gene 28 primers generally includes a first gene 28 primer and a second gene 28 primer. The first gene 28 primer can include the sequence 5'-GAC AAT ATC ATA TAC ATG GAA TGT G-3' (SEQ ID NO:1), and the second gene 28 primer can include the sequence 5'-GCG GTA GTA ACA GAG AAT TTC TT-3' (SEQ ID NO:2). A first gene 28 probe can include the sequence 5'-CGA AAA TCC AGA ATC GGA ACT TCT T-3' (SEQ ID NO:3), and the second gene 28 probe can include the sequence 5'-CCA TTA CAG TAA ACT TTA GGC GGT C-3' (SEQ ID NO:4).

A pair of gene 29 primers generally includes a first gene 29 primer and a second gene 29 primer. The first gene 29 primer can include the sequence 5'-TGT CCT AGA GGA GGT TTT ATC TG-3' (SEQ ID NO:5), and the second gene 29 primer can include the sequence 5'-CAT CGT CTG TAA GAC TTA ACC AG-3' (SEQ ID NO:6). A first gene 29 probe can include the sequence 5'-GGG AAA TCG AGA AAC CAC CCT ATC CGA C-3' (SEQ ID NO:7), and the second gene 29 probe can include the sequence 5'-AAG TTC GCG GTA TAA TTG TCA GTG GCG-3' (SEQ ID NO:8). In some aspects, one of the gene 28 or gene 29 primers can be labeled with a fluorescent moiety (either a donor or acceptor, as appropriate) and can take the place of the gene 28 or gene 29 probes, respectively.

The members of the pair of gene 28 probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the biological sample at a wavelength absorbed by the donor fluorescent moiety and visualizing and/or measuring the wavelength emitted by the acceptor fluorescent moiety (i.e., visualizing and/or measuring FRET). In another aspect, the detecting step includes quantitating the FRET. In yet another aspect, the detecting step can be performed after each cycling step (e.g., in real-time).

Generally, the presence of FRET within 50 cycles (e.g., 20, 25, 30, 35, 40, or 45 cycles) indicates the presence of a VZV infection in the individual. In addition, determining the melting temperature between one or both of the gene 28 probe(s) and the gene 28 amplification or similarly one or both of the gene 29 probe(s) and the gene 29 amplification product can confirm the presence or absence of the VZV.

Representative biological sample include dermal swabs, cerebrospinal fluid, ganglionic tissue, brain tissue, ocular fluid, blood, sputum, bronchio-alveolar lavage, bronchial aspirates, lung tissue, and urine. The above-described methods can further include preventing amplification of a contaminant nucleic acid. Preventing amplification can include performing the amplifying step in the presence of uracil and treating the biological sample with uracil-DNA glycosylase prior to amplifying.

In addition, the cycling step can be performed on a control sample. A control sample can include the same portion of the VZV gene 28 nucleic acid molecule. Alternatively, a control sample can include a nucleic acid molecule other than a VZV gene 28 nucleic acid molecule. Cycling steps can be performed on such a control sample using a pair of control primers and a pair of control probes. The control primers and probes are other than gene 28 primers and probes. One or more amplifying steps produces a control amplification product. Each of the control probes hybridizes to the control amplification product.

In another aspect of the invention, there are provided articles of manufacture, or kits. Kits of the invention can include a pair of gene 28 primers, and a pair of gene 28 probes, and a donor and corresponding acceptor fluorescent moieties. For example, the first gene 28 primer provided in a kit of the invention can have the sequence 5'-GAC AAT ATC ATA TAC ATG GAA TGT G-3' (SEQ ID NO:1) and the second gene 28 primer can have the sequence 5'-GCG GTA GTA ACA GAG AAT TTC TT-3' (SEQ ID NO:2). The first gene 28 probe provided in a kit of the invention can have the sequence 5'-CGA AAA TCC AGA ATC GGA ACT TCT T-3' (SEQ ID NO:3) and the second gene 28 probe can have the sequence 5'-CCA TTA CAG TAA ACT TTA GGC GGT C-3' (SEQ ID NO:4). Articles of manufacture of the invention can further or alternatively include a pair of gene 29 primers, a pair of gene 29 probes, and a donor and corresponding acceptor fluorescent moieties. For example, the first gene 29 primer provided in a kit of the invention can have the sequence 5'-TGT CCT AGA GGA GGT TTT ATC TG-3' (SEQ ID NO:5), and the second gene 29 primer can have the sequence 5'-CAT CGT CTG TAA GAC TTA ACC AG-3' (SEQ ID NO:6). The first gene 29 probe provided in a kit of the invention can have the sequence 5'-GGG AAA TCG AGA AAC CAC CCT ATC CGA C-3' (SEQ ID NO:7), and the second gene 29 probe can have the sequence 5'-AAG TTC GCG GTA TAA TTG TCA GTG GCG-3' (SEQ ID NO:8). Articles of manufacture can include fluorophoric moieties for labeling the probes or probes already labeled with donor and corresponding acceptor fluorescent moieties. The article of manufacture can also include a package insert having instructions thereon for using the primers, probes, and fluorophoric moieties to detect the presence or absence of VZV in a biological sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

A real-time assay for detecting VZV in a biological sample that is more sensitive than existing assays is described herein. Primers and probes for detecting VZV infections and articles of manufacture containing such primers and probes are provided by the invention. The increased sensitivity of real-time PCR for detection of VZV compared to other methods, as well as the improved features of real-time PCR including sample containment and real-time detection of the amplified product, make feasible the implementation of this technology for routine diagnosis of VZV infections in the clinical laboratory.

Varicella-Zoster Virus (VZV)

Varicella-zoster virus (VZV) is a human alphaherpesvirus (HHV-3) with a respiratory port of entry. VZV causes two distinct diseases, varicella and herpes zoster. Varicella infection causes the contagious childhood disease chicken pox. The initial infection results in virus growth in the regional lymph nodes that then feeds a primary viremia within 24 hours of contact. Subsequent sites of viral replication are established in organs such as the spleen and liver. A secondary lymphocyte-mediated viremia targets the subcutaneous epithelial cells where further replication causes deep necrotic lesions of the epidermis and dermis. A strong humoral and cellular immunity clears all actively replicating and antigen-presenting VZV infected cells from the bloodstream, skin and ganglia. Immunity is protective against subsequent exposure VZV. In addition, a varicella vaccine has been developed and is used to vaccinate children (e.g., between the ages of 12 months and 12 years) against chickenpox.

The varicella virus also can penetrate the peripheral nervous system and remain latent in dorsal root ganglia for many years. VZV activation in adults produces herpes zoster, commonly known as shingles. Herpes zoster infections present as a deep vascularized skin rash that is typically restricted to a dermatome. The latent state molecular biology of VZV, including viral load in ganglionic tissue is being investigated using, for example, PCR.

Each VZV virion contains one molecule of linear double-stranded DNA. VZV contains one of the smallest genomes in the herpesvirus family, with 125 kb of potential coding sequence. The VZV genome contains at least 69 functional genes based upon the identification of open reading frames (ORFs). The VZV genome is typical of the alphaherpesviruses with the ORFs arranged in the same order, position, and relative direction as the ORFs from, for example, pseudorabiesvirus (PRV), herpes simplex virus-1 (HSV-1) and equine herpesvirus (EHV-1).

VZV Nucleic Acids and Oligonucleotides

The invention provides methods to detect VZV by amplifying, for example, a portion of the VZV gene 28 or gene 29 nucleic acid. VZV nucleic acids other than those exemplified herein (e.g., other than gene 28 and gene 29) also can be used to detect VZV in a sample and are known to those of skill in the art. The nucleic acid sequence of the VZV genome, as well as VZV gene 28 (encoding DNA polymerase) and gene 29 (encoding a single-stranded binding protein), are available (see, for example, GenBank Accession Nos. X04370, M14891 and M16612). Note that gene 28 has been referred to as UL30 in the literature while gene 29 has been referred to as UL29. Specifically, primers and probes to amplify and detect VZV gene 28 nucleic acid molecules are provided by the invention as are primers and probes to amplify and detect VZV gene 29 nucleic acid molecules.

Primers that amplify a VZV nucleic acid molecule, e.g., VZV gene 28 or gene 29, can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 30 nucleotides in length.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of VZV strains based on either absolute hybridization of different pairs of probes corresponding to the particular VZV strain to be distinguished or differential melting temperatures between, for example, members of a pair of probes and each amplification product corresponding to a VZV strain to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 30 nucleotides in length.

Constructs of the invention include vectors containing a VZV nucleic acid molecule, e.g., VZV gene 28 or gene 29, or fragment thereof and can be used, for example, as a control template nucleic acid molecule. Vectors suitable for use in the present invention are commercially available and/or produced by recombinant DNA technology methods routine in the art. VZV gene 28 or gene 29 nucleic acid molecules can be obtained, for example, by chemical synthesis, direct cloning from VZV, or by PCR amplification. A VZV nucleic acid molecule or fragments thereof can be operably linked to a promoter or other regulatory element such as an enhancer sequence, a response element, or an inducible element that modulates expression of the VZV nucleic acid molecule. As used herein, operably linking refers to connecting a promoter and/or other regulatory elements to a VZV nucleic acid molecule in such a way as to permit and/or regulate expression of the VZV nucleic acid molecule. A promoter that does not normally direct expression of VZV gene 28 or gene 29 can be used to direct transcription of a gene 28 or gene 29 nucleic acid using, for example, a viral polymerase, a bacterial polymerase, or a eukaryotic RNA polymerase II. Alternatively, the gene 28 or gene 29 native promoter can be used to direct transcription of a gene 28 or gene 29 nucleic acid, respectively, using, for example, a VZV RNA polymerase enzyme. In addition, operably linked can refer to an appropriate connection between a VZV gene 28 or gene 29 promoter or regulatory element and a heterologous coding sequence (i.e., a non-gene 28 or gene 29 coding sequence, for example, a reporter gene) in such a way as to permit expression of the heterologous coding sequence.

Constructs suitable for use in the methods of the invention typically include, in addition to VZV gene 28 or gene 29 nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing VZV gene 28 or gene 29 nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within VZV gene 28 or gene 29. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the VZV template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the VZV nucleic acid. The temperature for annealing is usually from about 35° C. to about 65° C. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature generally ranges from about 40° to 80° C.).

PCR assays can employ VZV nucleic acid such as DNA or RNA, including messenger RNA (mRNA). The template nucleic acid need not be purified; it may be a minor fraction of a complex mixture, such as VZV nucleic acid contained in human cells. DNA or RNA may be extracted from a biological sample such as dermal swabs, cerebrospinal fluid, ganglionic tissue, brain tissue, ocular fluid, blood, sputum, bronchio-alveolar lavage, bronchial aspirates, lung tissue, and urine by routine techniques such as those described in *Diagnostic Moleculear Microbiology: Principles and Applications* (Persing et al. (eds), 1993, American Society for Microbiology, Washington D.C). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5–1.0 $\mu$g denatured template DNA, 50 pmoles of each oligonucleotide primer, 2.5 U of Taq polymerase, and 10% DMSO). The reactions usually contain 150 to 320 $\mu$M each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target VZV nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor and a corresponding acceptor fluorescent moiety are positioned within a certain distance of each other, energy transfer takes place between the two fluorescent moieties that can be visualized or otherwise detected and/or quantitated. As used herein, two oligonucleotide probes, each containing a fluorescent moiety, can hybridize to an amplification product at particular positions determined by the complementarity of the oligonucleotide probes to the VZV target nucleic acid sequence. Upon hybridization of the oligonucleotide probes to the amplification product nucleic acid at the appropriate positions, a FRET signal is generated.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives.

Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of VZV

Detection of VZV can be by a number of testing modalities and from a number of specimen types. Standard laboratory diagnosis has been obtained by culture of the virus in diploid fibroblasts seeded into shell vial cell cultures or by immunostaining viral antigens in infected cells collected by swabs of vesicles from patients. In addition, serologic assays for immunoglobulin G or A class antibodies also are used to detect and diagnose VZV, although serological assays may be less useful for diagnosing VZV infections in view of available varicella vaccinations. See, for example, Brinker & Doern, 1993, *Diagn. Microbiol Infect. Dis.,* 17:75–77; Coffin & Hodinka, 1995, *J. Clin. Microbiol.,* 33:2792–2795; McCarter & Ratkiewicz, 1998, *Am. J. Clin. Pathol.,* 109:631–633; Shirm et al., 1989, *J. Med. Virol.,* 28:1–6; and Sauerbrei et al., 1999, *J. Clin. Virol.,* 14:31–6 for detection of VZV.

Conventional PCR methods also have been used to detect VZV. Conventional PCR-based amplification is generally followed by transfer to a solid support and detection using a labeled probe (e.g., a Southern or Northern blot). These methods are labor intensive and frequently require more than one day to complete. Additionally, the manipulation of amplification products for the purposes of detection (e.g., by blotting) increases the risk of carry-over contamination and false positives. By using commercially available real-time PCR instrumentation (e.g., LightCycler™, Roche Molecular Biochemicals, Indianapolis, Ind.), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The present invention provides methods for detecting the presence or absence of VZV in a biological sample from an individual. Methods provided by the invention avoid problems of sample contamination, false negatives, and false positives. The methods include performing at least one cycling step that includes amplifying a VZV portion of a gene 28 nucleic acid molecule from a biological sample using a pair of gene 28 primers. Each of the gene 28 primers anneals to a target within or adjacent to a VZV gene 28 nucleic acid molecule such that at least a portion of the amplification product contains nucleic acid sequence corresponding to gene 28 and, more importantly, such that the amplification product contains the nucleic acid sequences that are complementary to the gene 28 probes. The gene 28 amplification product is produced provided that VZV nucleic acid is present. Each cycling step further includes hybridizing a pair of gene 28 probes to the gene 28 amplification product. According to the invention, one of the gene 28 probes is labeled with a donor fluorescent moiety and the other is labeled with a corresponding acceptor fluorescent moiety. The presence or absence of FRET between the donor fluorescent moiety of the first gene 28 probe and the corresponding acceptor fluorescent moiety of the second gene 28 probe is detected upon hybridization of both gene 28 probes to the gene 28 amplification product.

Each cycling step includes an amplification step and a hybridization step, and each cycling step is usually followed by a FRET detecting step. Multiple cycling steps are performed, preferably in a thermocycler. The above-described methods for detecting VZV in a biological sample using primers and probes directed toward gene 28 also can be performed using other VZV gene-specific primers and probes, for example, gene 29-specific primers and gene 29-specific probes.

As used herein, "amplifying" refers to the process of synthesizing nucleic acid molecules that are complementary to one or both strands of a template nucleic acid molecule (e.g., VZV gene 28 or gene 29 nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

If amplification of VZV nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of VZV in the biological sample, and the absence of FRET indicates the absence of VZV in the biological sample. Inadequate specimen collection, transportation delays, inappropriate transportation conditions, or use of certain collection swabs (calcium alginate or aluminum shaft) are all conditions that can affect the success and/or accuracy of a test result, however.

Using the methods disclosed herein, detection of FRET within 30 cycling steps is indicative of a VZV infection. Samples in which FRET is detected after more than 30 cycling steps also is indicative of a VZV infection, but can be evaluated for VZV infection, if desired, using a method of the invention with a different gene target or an assay other than the real-time PCR described herein. The cycle number at which FRET is detectable can be correlated with the amount of VZV in a biological sample and, hence, in the individual (e.g., viral load).

Methods of the invention also can be used for VZV vaccine efficacy studies or epidemiology studies. For example, an attenuated VZV in a varicella vaccine can be detected using the methods of the invention during the time when virus is still present in an individual. For such vaccine efficacy studies, the methods of the invention can be used to determine, for example, the replicating ability or persistence of an attenuated virus used in a vaccine, or can be performed in conjunction with an additional assay such as a serologic assay to monitor an individual's immune response to such a vaccine. In addition, methods of the invention can be used to distinguish one VZV strain from another for epidemiology studies of, for example, the origin or severity of an outbreak of varicella (chickenpox) and/or herpes zoster (shingles).

Representative biological samples that can be used in practicing the methods of the invention include dermal swabs, cerebrospinal fluid, ganglionic tissue, brain tissue, ocular fluid, blood, sputum, bronchio-alveolar lavage, bronchial aspirates, lung tissue, and urine. Biological sample collection and storage methods are known to those of skill in the art. Biological samples can be processed (e.g., by nucleic acid extraction methods and/or kits known in the art) to release VZV nucleic acid or in some cases, the biological sample is contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Ssimilarly, by detecting the temperature at which signal is generated, the annealing temperature of probes can be determined. The melting temperature(s) of the gene 28 or gene 29 probes from the respective amplification product can confirm the presence or absence of VZV in the sample.

Within each thermocycler run, control samples are cycled as well. Positive control samples can amplify VZV nucleic acid control template (other than gene 28 or gene 29) using, for example, control primers and control probes. Positive control samples can also amplify, for example, a plasmid construct containing VZV gene 28 or gene 29 nucleic acid molecule. Such a plasmid control can be amplified internally (e.g., within the biological sample) or in a separate sample run side-by-side with the patients' samples. Each thermocycler run should also include a negative control that, for example, lacks VZV template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Although conventional PCR methods in conjunction with FRET technology can be used to practice the methods of the invention, in one embodiment, a LightCycler™ instrument is used. A detailed description of the LightCycler™ System and real-time and on-line monitoring of PCR can be found on Roche's website. The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LightCycler™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LightCycler™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LightCycler™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10–100 msec. After each cycling step, a quantitative display of fluorescence vs. cycle number can be continually updated for all samples. The data generated can be stored for further analysis.

The fluorescent formats currently used as reporters in the LightCycler™ System are the double-stranded DNA binding dye SYBR Green I, and fluorescent labels attached to hybridization probes. Whereas signal development in the presence of the SYBR Green I dye is dependent on the formation of double-stranded DNA (regardless of the DNA sequence), signal from hybridization requires the production of sequence-specific probes. Hybridization probes are typically labeled with two different fluorescent moieties and hybridize in close proximity to each other in a target DNA molecule (e.g., an amplification product). A donor fluorescent moiety, for example, fluorescein, is excited at 470 nm by the light source of the LightCycler™ Instrument. The fluorescein can then transfer its energy to an acceptor fluorescent moiety, for example, LightCycler™-Red 640 (LC™-Red 640) or LightCycler™-Red 705 (LC™-Red 705), during FRET. The acceptor fluorescent moiety then emits light of a longer wavelength, which is then detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of VZV genomes).

In another embodiment, and ABI PRISM® 7700 Sequence Detection System (Applied Biosystems, Foster City, Calif.) also is suitable for performing the methods described herein for detecting VZV. Information on PCR amplification and detection using an ABI PRISM® 770 system can be found on Applied Biosystems' website. The present invention, however, is not limited by the configuration of a commercially available instrument.

Articles of Manufacture

The invention further provides for articles of manufacture to detect VZV. An article of manufacture according to the present invention can include primers and probes used to detect VZV, together with suitable packaging materials. Representative primers and probes for detection of VZV are complementary to VZV gene 28 or gene 29 nucleic acid molecules. Methods of designing primers and probes are disclosed herein, and representative examples of primers and probes that amplify and hybridize to VZV gene 28 or gene 29 nucleic acid molecules are provided.

Articles of manufacture of the invention also can include one or more fluorscent moieties for labeling the probes or, alternatively, the probes supplied with the kit can be labeled. For example, an article of manufacture may include a donor fluorescent moiety for labeling one of the gene 28 or gene 29 probes and an acceptor fluorescent moiety for labeling the other gene 28 or gene 29 probe. Examples of suitable FRET donor fluorescent moieties and corresponding acceptor fluorescent moieties are provided above.

Articles of manufacture of the invention also can contain a package insert having instructions thereon for using the gene 28 primers and probes or gene 29 primers and probes to detect VZV in a biological sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Specimens, Cell Cultures, and Nucleic Acid Extractions

Dermal swabs (n=253) from patients suspected of having VZV infections were extracted and inoculated into MRC-5 shell vial cell cultures as previously described for HSV (Gleaves et al., 1985, *J. Clin. Microbiol.*, 21:29–32). Nucleic acids were extracted (IsoQuick, Orca Research, Inc., Bothell, Wash.) and amplified by LightCycler™ PCR (Espy et al., 2000, *J. Clin. Microbiol.*, 38:795–799).

Example 2

LightCycler™ PCR

The LightCycler™ instrument can amplify target nucleic acids within about 30–40 min and monitors the development of PCR product by fluorescence assay after each cycling step (amplification and hybridization). All samples were amplified by LightCycler™ PCR with primers directed to both gene 28 and gene 29. PCR primers for detection of VZV DNA using gene 28 were designed using the OLIGO program and had the following sequences: sense, 5'-GAC AAT ATC ATA TAC ATG GAA TGT G-3' (SEQ ID NO:1); antisense, 5'-GCG GTA GTA ACA GAG AAT TTC TT-3' (SEQ ID NO:2); and probes 5'-CGA AAA TCC AGA ATC GGA ACT TCT T-fluorescein-3' (SEQ ID NO:3) and 5'-Red 640-CCA TTA CAG TAA ACT TTA GGC GGT C-phosphate-3' (SEQ ID NO:4). Amplification of VZV using such primers directed toward gene 28 generated a 282 bp amplification product (Saverbrei et al., 1999, *J. Clin. Virol.*, 14:31–6). A PCR master mix (see Espy et al., 2000, *J. Clin. Microbiol.*, 38:795–9) was modified for the VZV gene 28 LightCycler™ Assay by eliminating DMSO and using 4 mM MgCl and 1 μM gene 28 primers. Samples underwent 45 cycles of: denaturation at about 95° C. immediately followed by primer annealing to the template nucleic acid for about 12 secs at about 55° C., and elongation of the newly-synthesized strands at about 72° C. for about 12 secs.

Primers and probes for detection of VZV DNA using gene 29 were designed using the OLIGO software (Molecular Biology Insights, Inc., Cascade, Colo.) and had the following sequences: sense, 5'-TGT CCT AGA GGA GGT TTT ATC TG-3' (SEQ ID NO:5); antisense, 5'-CAT CGT CTG TAA GAC TTA ACC AG-3' (SEQ ID NO:6); and probes 5'-GGG AAA TCG AGA AAC CAC CCT ATC CGA C-fluorescein-3' (SEQ ID NO:7) and 5'-Red 640-AA GTT CGC GGT ATA ATT GTC AGT GGC G-phosphate-3' (SEQ ID NO:8). Amplification using such gene 29 primers produced an amplification product of 202 bp. The PCR master mix (see Espy et al., 2000, *J. Clin. Microbiol.*, 38:795–9) was modified for the VZV gene 29 LightCycler™ Assay by using 4 mM MgCl, 1 μM gene 29 primers and 3% dimethylsulfoxide. The thermocycling program for gene 29 was the same as described above for gene 28.

Both sets of hybridization probes (i.e., gene 28 and gene 29 probes) contained a donor fluorophore (fluorescein) on the 3'-end of one probe, which when excited by an external light source, emitted light that was absorbed by a corresponding acceptor fluorophore (LC-Red 640) at the 5'-end of the second hybridization probe. Both the gene 28 and gene 29 LightCycler™ assays detected ≧20 genomic copies of VZV.

Example 3

Detection of VZV

Of 253 dermal specimens, VZV was detected in 23 (9.1%) by shell vial cell cultures, while 44 (17.4%) (gene 28) and 50 (19.7%) (gene 29) were detected by LightCycler™ PCR tests (Table 1). Twenty-one of 44 (47.7%) (gene 28) and 27 of 50 (54.0%) (gene 29) specimens were exclusively positive by LightCycler™ PCR; the shell vial cell culture assay was never positive when DNA amplification was negative (specificity, 100%). VZV DNA was detected in 39 of 44 (88.6%)(gene 28) and 39 of 50 (78.0%) (gene 29) total specimens positive during cycles 10 through 30 by the LightCycler™ assay. In addition, of the 23 total specimens positive by the shell vial assay, VZV DNA was detected by both gene 28 and gene 29 LightCycler™ assays in these samples by cycle 26, indicating a direct relationship between the capability of culturing the virus by the shell vial assay and the recognition of amplified VZV product in the early cycles of LightCycler™ PCR.

TABLE 1

Detection of VZV DNA by LightCycler ™ PCR and by shell vial cell culture

| | Number of specimens positive | | |
|---|---|---|---|
| | LightCycler ™ | | |
| Cycle number | gene 28 | gene 29 | Shell vial cell culture |
| 0–30 | 39 | 39 | 23 |
| 31 | 0 | 1 | 0 |
| 32 | 0 | 0 | 0 |
| 33 | 1 | 2 | 0 |
| 34 | 3 | 4 | 0 |
| 35 | 1 | 3 | 0 |
| 36 | 0 | 1 | 0 |
| Total | 44 | 50 | 23 |

Of the 50 specimens examined using LightCycler™ PCR and primers and probes directed toward gene 29, FRET was detected in 11 samples between cycles 30 and 36. VZV DNA was never exclusively detected using only primers and probes directed toward gene 28 in the absence of a positive LightCycler™ result using primers and probes directed toward gene 29. Specificity of the LightCycler™ assay was further demonstrated by melting point analysis, which was performed with all samples from which a fluorescent signal was generated. All positive samples had a melting curve consistent with the positive VZV control.

Primers and probes directed to gene 29 detected 50 specimens containing VZV DNA, whereas 44 specimens were positive for VZV using primers and probes directed toward gene 28. In routine laboratory practice, primers and probes directed to gene 28 may be used, even though amplification and detection of VZV using primers and probes directed toward gene 29 was more sensitive than that using primers and probes directed toward gene 28. Forty-four samples containing VZV were positive by PCR directed to both gene 28 and gene 29. For clinical implementation, detection using PCR amplification directed to either gene 28 or gene 29 is much improved over the current assays, although detection of VZV using primers and probes directed toward gene 29 is more sensitive. Thus, gene 28 or gene 29 can be amplified and detected individually or in combination to detect VZV.

The assay described herein exhibited specificity for VZV since VZV-specific primers and probes amplified only VZV DNA. DNA from herpes simplex virus (HSV), cytomegalovirus (CMV), Epstein-Barr virus (EBV), and human herpesviruses 6, 7, and 8 were tested with VZV-specific primers and probes and were uniformly negative. Significantly, there was no cross reaction in fluorescence signal between VZV- and HSV-positive samples.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of VZV in a biological sample from an individual, said method comprising:

performing at least one cycling step, wherein a cycling step comprises an amplifying step and a hybridizing step, wherein said amplifying step comprises contacting said sample with a pair of gene 28 primers to produce a gene 28 amplification product if a VZV gene 28 nucleic acid molecule is present in said sample, wherein said pair of gene 28 primers comprises a first gene 28 primer and a second gene 28 primer, wherein said first gene 28 primer is no more than 30 nucleotides in length and comprises the sequence 5'-GAC AAT ATC ATA TAC ATG GAA TGT G-3' (SEQ ID NO:1), wherein said hybridizing step comprises contacting said sample with a pair of gene 28 probes, wherein the members of said pair of gene 28 probes hybridize to said amplification product within no more than five nucleotides of each other, wherein a first gene 28 probe of said pair of gene 28 probes is labeled with a donor fluorescent moiety and wherein a second gene 28 probe of said pair of gene 28 probes is labeled with a corresponding acceptor fluorescent moiety; and detecting the presence or absence of fluorescence resonance energy transfer (FRET) between said donor fluorescent moiety of said first gene 28 probe and said acceptor fluorescent moiety of said second gene 28 probe, wherein the presence of FRET is indicative of the presence of VZV in said biological sample, and wherein the absence of FRET is indicative of the absence of VZV in said biological sample.

2. The method of claim 1, wherein said second gene 28 primer comprises the sequence 5'-GCG GTA GTA ACA GAG AAT TTC TT-3' (SEQ ID NO:2).

3. A method for detecting the presence or absence of VZV in a biological sample from an individual, said method comprising:

performing at least one cycling step, wherein a cycling step comprises an amplifying step and a hybridizing step, wherein said amplifying step comprises contacting said sample with a pair of gene 28 primers to produce a gene 28 amplification product if a VZV gene 28 nucleic acid molecule is present in said sample, wherein said pair of gene 28 primers comprises a first gene 28 primer and a second gene 28 primer, wherein said second gene 28 primer is no more than 30 nucleotides in length and comprises the sequence 5'-GCG GTA GTA ACA GAG AAT TTC TT -3' (SEQ ID NO:2), wherein said hybridizing step comprises contacting said sample with a pair of gene 28 probes, wherein the members of said pair of gene 28 probes hybridize to said amplification product within no more than five nucleotides of each other, wherein a first gene 28 probe of said pair of gene 28 probes is labeled with a donor fluorescent moiety and wherein a second gene 28 probe of said pair of gene 28 probes is labeled with a corresponding acceptor fluorescent moiety; and detecting the presence or absence of fluorescence resonance energy transfer (FRET) between said donor fluorescent moiety of said first gene 28 probe and said acceptor fluorescent moiety of said second gene 28 probe, wherein the presence of FRET is indicative of the presence of VZV in said biological sample, and wherein the absence of FRET is indicative of the absence of VZV in said biological sample.

4. The method of claim 3, wherein said first gene 28 primer comprises the sequence 5'-GAC AAT ATC ATA TAC ATG GAA TGT G-3' (SEQ ID NO:1).

5. A method for detecting the presence or absence of VZV in a biological sample from an individual, said method comprising:

performing at least one cycling step, wherein a cycling step comprises an amplifying step and a hybridizing step, wherein said amplifying step comprises contacting said sample with a pair of gene 28 primers to produce a gene 28 amplification product if a VZV gene 28 nucleic acid molecule is present in said sample, wherein said hybridizing step comprises contacting said sample with a pair of gene 28 probes, wherein the members of said pair of gene 28 probes hybridize to said amplification product within no more than five nucleotides of each other, wherein a first gene 28 probe of said pair of gene 28 probes is labeled with a donor fluorescent moiety and wherein a second gene 28 probe of said pair of gene 28 probes is labeled with a corresponding acceptor fluorescent moiety, wherein said first gene 28 probe is no more than 30 nucleotides in length and comprises the sequence 5'-CGA AAA TCC AGA ATC GGA ACT TCT T-3' (SEQ ID NO:3); and detecting the presence or absence of fluorescence resonance energy transfer (FRET) between said donor fluorescent moiety of said first gene 28 probe and said acceptor fluorescent moiety of said second gene 28 probe, wherein the presence of FRET is indicative of the presence of VZV in said biological sample, and wherein the absence of FRET is indicative of the absence of VZV in said biological sample.

6. The method of claim 5, wherein said second gene 28 probe comprises the sequence 5'-CCA TTA CAG TAA ACT TTA GGC GGT C-3' (SEQ ID NO:4).

7. A method for detecting the presence or absence of VZV in a biological sample from an individual, said method comprising:

performing at least one cycling step, wherein a cycling step comprises an amplifying step and a hybridizing step, wherein said amplifying step comprises contacting said sample with a pair of gene 28 primers to produce a gene 28 amplification product if a VZV gene 28 nucleic acid molecule is present in said sample, wherein said hybridizing step comprises contacting said sample with a pair of gene 28 probes, wherein the members of said pair of gene 28 probes hybridize to said amplification product within no more than five nucleotides of each other, wherein a first gene 28 probe of said pair of gene 28 probes is labeled with a donor fluorescent moiety and wherein a second gene 28 probe of said pair of gene 28 probes is labeled with a corresponding acceptor fluorescent moiety, wherein said second gene 28 probe is no more than 30 nucleotides in length and comprises the sequence 5'-CCA TTA CAG TAA ACT TTA GGC GGT C-3' (SEQ ID NO:4); and detecting the presence or absence of fluorescence resonance energy transfer (FRET) between said donor fluorescent moiety of said first gene 28 probe and said acceptor fluorescent moiety of said second gene 28 probe, wherein the presence of FRET is indicative of the presence of VZV in said biological sample, and wherein the absence of FRET is indicative of the absence of VZV in said biological sample.

8. The method of claim 7, wherein said first gene 28 probe comprises the sequence 5'-CGA AAA TCC AGA ATC GGA ACT TCT T-3' (SEQ ID NO:3).

9. The method of claim 1, 3, 5, or 7, wherein the presence of said FRET within 50 cycling steps is indicative of the presence of a VZV infection in said individual.

10. The method of claim 1, 3, 5, or 7, wherein the presence of said FRET within 40 cycling steps is indicative of the presence of a VZV infection in said individual.

11. The method of claim 1, 3, 5, or 7, wherein the presence of said FRET within 30 cycling steps is indicative of the presence of a VZV infection in said individual.

12. The method of claim 1, 3, 5, or 7, wherein said cycling step is performed on a control sample.

13. The method of claim 12, wherein said control sample comprise said VZV gene 28 nucleic acid molecule.

14. The method of claim 1, 3, 5, or 7, wherein said cycling step uses a pair of control primers and a pair of control probes, wherein said control primers and said control probes are other than said gene 28 primers and said gene 28 probes, wherein a control amplification product is produced if control template is present in said sample, wherein said control probes hybridize to said control amplification product.

15. The method of claim 1, 3, 5, or 7, further comprising:
performing at least one cycling step, wherein said cycling step comprises an amplifying step and a hybridizing step, wherein said amplifying step comprises contacting said sample with a pair of gene 29 primers to produce a gene 29 amplification product if a VZV gene 29 nucleic acid molecule is present in said sample, wherein said hybridizing step comprises contacting said sample with a pair of gene 29 probes, wherein the members of said pair of gene 29 probes hybridize within no more than five nucleotides of each other, wherein a first gene 29 probe of said pair of gene 29 probes is labeled with a donor fluorescent moiety and wherein a second gene 29 probe of said pair of gene 29 probes is labeled with a corresponding acceptor fluorescent moiety; and
detecting the presence or absence of FRET between said donor fluorescent moiety of said first gene 29 probe and said acceptor fluorescent moiety of said second gene 29 probe upon hybridization of said pair of gene 29 probes to said targets.

16. The method of claim 15, wherein said pair of gene 29 primers comprises a first gene 29 primer and a second gene 29 primer, wherein said first gene 29 primer comprises the sequence 5'-TGT CCT AGA GGA GGT TTT ATC TG-3' (SEQ ID NO:5), and wherein said second gene 29 primer comprises the sequence 5'-CAT CGT CTG TAA GAC TTA ACC AG-3' (SEQ ID NO:6).

17. The method of claim 15, wherein said first gene 29 probe comprises the sequence 5'-GGG AAA TCG AGA AAC CAC OCT ATC CGA C-3' (SEQ ID NO:7), and wherein said second gene 29 probe comprises the sequence 5'-AAG TTC GCG GTA TAA TTG TCA GTG GCG-3' (SEQ ID NO:8).

18. A method for detecting the presence or absence of VZV in a biological sample from an individual, said method comprising:
performing at least one cycling step, wherein a cycling step comprises an amplifying step and a hybridizing step, wherein said amplifying step comprises contacting said sample with a pair of gene 29 primers to produce a gene 29 amplification product if a VZV gene 29 nucleic acid molecule is present in said sample, wherein said pair of gene 29 primers comprises a first gene 29 primer and a second gene 29 primer, wherein said first gene 29 primer is no more than 30 nucleotides in length and comprises the sequence 5'-TGT CCT AGA GGA GGT TTT ATC TG-3' (SEQ ID NO:5), wherein said hybridizing step comprises contacting said sample with a pair of gene 29 probes, wherein the members of said pair of gene 29 probes hybridize within no more than five nuoleotides of each other, wherein a first gene 29 probe of said pair of gene 29 probes is labeled with a donor fluorescent moiety and wherein a second gene 29 probe of said pair of gene 29 probes is labeled with a corresponding acceptor fluorescent moiety; and
detecting the presence or absence of fluorescence resonance energy transfer (FRET) between said donor fluorescent moiety of said first gene 29 probe and said acceptor fluorescent moiety of said second gene 29 probe upon hybridization of said pair of gene 29 probes to said targets,
wherein the presence of FRET is indicative of the presence of VZV in said biological sample, and wherein the absence of FRET is indicative of the absence of VZV in said biological sample.

19. The method of claim 18, wherein said second gene 29 primer comprises the sequence 5'-CAT CGT CTG TAA GAC TTA ACC AG-3' (SEQ ID NO:6).

20. A method for detecting the presence or absence of VZV in a biological sample from an individual, said method comprising:
performing at least one cycling step, wherein a cycling step comprises an amplifying step and a hybridizing step, wherein said amplifying step comprises contacting said sample with a pair of gene 29 primers to produce a gene 29 amplification product if a VZV gene 29 nucleic acid molecule is present in said sample, wherein said pair of gene 29 primers comprises a first gene 29 primer and a second gene 29 primer, wherein said second gene 29 primer is no more than 30 nucleotides in length and comprises the sequence 5'-CAT CGT CTG TAA GAC TTA ACC AG-3'(SEQ ID NO:6), wherein said hybridizing step comprises contacting said sample with a pair of gene 29 probes, wherein the members of said pair of gene 29 probes hybridize within no more than five nucleotides of each other, wherein a first gene 29 probe of said pair of gene 29 probes is labeled with a donor fluorescent moiety and wherein a second gene 29 probe of said pair of gene 29 probes is labeled with a corresponding acceptor fluorescent moiety; and
detecting the presence or absence of fluorescence resonance energy transfer (FRET) between said donor fluorescent moiety of said first gene 29 probe and said acceptor fluorescent moiety of said second gene 29 probe upon hybridization of said pair of gene 29 probes to said targets,
wherein the presence of FRET is indicative of the presence of VZV in said biological sample, and wherein the absence of FRET is indicative of the absence of VZV in said biological sample.

21. The method of claim 20, wherein said first gene 29 primer comprises the sequence 5'-TGT CCT AGA GGA GGT TTT ATC TG-3' (SEQ ID NO:5).

22. A method for detecting the presence or absence of VZV in a biological sample from an individual, said method comprising:
performing at least one cycling step, wherein a cycling step comprises an amplifying step and a hybridizing step, wherein said amplifying step comprises contacting said sample with a pair of gene 29 primers to produce a gene 29 amplification product if a VZV gene 29 nucleic acid molecule is present in said sample, wherein said hybridizing step comprises contacting said sample with a pair of gene 29 probes, wherein the members of said pair of gene 29 probes hybridize within no more than five nucleotides of each other, wherein a first gene 29 probe of said pair of gene 29 probes is labeled with a donor fluorescent moiety and wherein a second gene 29 probe of said pair of gene 29 probes is labeled with a corresponding acceptor fluorescent moiety, wherein said first gene 29 probe is no more than 30 nucleotides in length and comprises the sequence 5'-GGG AAA TCG AGA AAC CAC CCT ATC CGA C-3' (SEQ ID NO:7); and detecting the presence or absence of fluorescence resonance energy transfer (FRET) between said donor fluorescent moiety of said first gene 29 probe and said acceptor fluorescent moiety of said second gene 29 probe upon hybridization of said pair of gene 29 probes to said targets, wherein the presence of FRET is indicative of the presence of VZV in said biological sample, and wherein the absence of FRET is indicative of the absence of VZV in said biological sample.

23. The method of claim 22, wherein said second gene 29 probe comprises the sequence 5'-AAG TTC GCG GTA TAA TTG TCA GTG GCG-3' (SEQ ID NO:8).

24. A method for detecting the presence or absence of VZV in a biological sample from an individual, said method comprising:

performing at least one cycling step, wherein a cycling step comprises an amplifying step and a hybridizing step, wherein said amplifying step comprises contacting said sample with a pair of gene 29 primers to produce a gene 29 amplification product if a VZV gene 29 nucleic acid molecule is present in said sample, wherein said hybridizing step comprises contacting said sample with a pair of gene 29 probes, wherein the members of said pair of gene 29 probes hybridize within no more than five nucleotides of each other, wherein a first gene 29 probe of said pair of gene 29 probes is labeled with a donor fluorescent moiety and wherein a second gene 29 probe of said pair of gene 29 probes is labeled with a corresponding acceptor fluorescent moiety, wherein said second gene 29 probe is no more than 30 nucleotides in length and comprises the sequence 5'-AAG TTC GCG GTA TAA TTG TCA GTG GCG-3' (SEQ ID NO:8); and detecting the presence or absence of fluorescence resonance energy transfer (FRET) between said donor fluorescent moiety of said first gene 29 probe and said acceptor fluorescent moiety of said second gene 29 probe upon hybridization of said pair of gene 29 probes to said targets, wherein the presence of FRET is indicative of the presence of VZV in said biological sample, and wherein the absence of FRET is indicative of the absence of VZV in said biological sample.

25. The method of claim 24, wherein said first gene 29 probe comprises the sequence 5'-GGG AAA TCG AGA AAC CAC CCT ATC CGA C-3' (SEQ ID NO:7).

26. The method of claim 18, 20, 22, or 24, wherein the presence of said FRET within 50 cycling steps is indicative of the presence of a VZV infection in said individual.

27. The method of claim 18, 20, 22, or 24, wherein the presence of said FRET within 40 cycling steps is indicative of the presence of a VZV infection in said individual.

28. The method of claim 18, 20, 22, or 24, wherein the presence of said FRET within 30 cycling steps is indicative of the presence of a VZV infection in said individual.

29. The method of claim 18, 20, 22, or 24, wherein said cycling step is performed on a control sample.

30. The method of claim 29, wherein said control sample comprises said VZV gene 29 nucleic acid molecule.

31. The method of claim 18, 20, 22, or 24, wherein said cycling step uses a pair of control primers and a pair of control probes, wherein said control primers and said control probes are other than said gene 29 primers and said gene 29 probes, wherein a control amplification product is produced if control template is present in said sample, wherein said control probes hybridize to said control amplification product.

32. The method of claim 1, 3, 5, 7, 18, 20, 22, or 24, wherein the members of said pair of probes hybridize within no more than two nucleotides of each other.

33. The method of claim 1, 3, 5, 7, 18, 20, 22, or 24, wherein the members of said pair of probes hybridize within no more than one nucleotide of each other.

34. The method of claim 1, 3, 5, 7, 18, 20, 22, or 24, wherein said donor fluorescent moiety is fluorescein.

35. The method of claim 1, 3, 5, 7, 18, 20, 22, or 24, wherein said detecting step comprises exciting said biological sample at a wavelength absorbed by said donor fluorescent moiety and visualizing and/or measuring the wavelength emitted by said acceptor fluorescent moiety.

36. The method of claim 1, 3, 5, 7, 18, 20, 22, or 24, wherein said detecting comprises quantitating said FRET.

37. The method of claim 1, 3, 5, 7, 18, 20, 22, or 24, wherein said detecting step is performed after each cycling step.

38. The method of claim 1, 3, 5, 7, 18, 20, 22, or 24, wherein said detecting step is performed in real time.

39. The method of claim 1, 3, 5, 7, 18, 20, 22, or 24, further comprising determining the melting temperature between one or both of said probe(s) and said amplification product, wherein said melting temperature confirms said presence or said absence of said VZV or VZV.

40. The method of claim 1, 3, 5, 7, 18, 20, 22, or 24, further comprising preventing amplification of a contaminant nucleic acid.

41. The method of claim 40, wherein said preventing comprises amplifying step in the presence of uracil.

42. The method of claim 41, wherein said preventing further comprises treating said biological sample with uracil-DNA glycosylase prior to a first amplification step.

43. The method of claim 1, 3, 5, 7, 18, 20, 22, or 24, wherein said biological sample is selected from the group consisting of dermal swabs, cerebrospinal fluid, ganglionic tissue, brain tissue, ocular fluid, blood, sputum, bronchioalveolar lavage, bronchial aspirates, lung tissue, and urine.

* * * * *

UNITED STATES PATENT AND TRADEMARK OFFICE
CERTIFICATE OF CORRECTION

PATENT NO. : 6,849,407 B2
DATED : February 1, 2005
INVENTOR(S) : Thomas F. Smith, James R. Uhl and Mark J. Espy It is certified that error appears in the above-identified patent and that said Letters Patent is hereby corrected as shown below:

Title page,
Item [56], References Cited, OTHER PUBLICATIONS,
"Davison et al." reference, please delete "19986" and insert -- 1986 -- therefor;
"Brinker and Doern" reference, please delete "Comparsion" and insert -- Comparison -- therefor;
"de Jong et al." reference, please delete "3568" and insert -- 2568 -- therefor;
"van Gelderen et al." reference, please delete "buttoms" and insert -- buttons -- therefor;
"Yamamoto and Nakamura" reference, please delete "cerbrospinal" and insert
-- cerebrospinal -- therefor;
"Arthur et al." reference, please delete "faccium" and insert -- faecium -- therefor;
"Patel et al.", reference, please delete "faecium" and insert -- faecalis -- therefor;
please delete "Reischul" and insert -- Reischl -- therefor;
"Ramotar et al." reference, please delete "Eschericha" and insert -- Escherichia -- therefor;

Column 24,
Line 47, after "comprises" please insert -- performing said --.

Signed and Sealed this

Sixth Day of December, 2005

JON W. DUDAS
*Director of the United States Patent and Trademark Office*